United States Patent
Brooks et al.

(10) Patent No.: US 6,849,060 B1
(45) Date of Patent: Feb. 1, 2005

(54) PARTICLE DELIVERY DEVICE

(75) Inventors: Emily L. Brooks, London (GB); Stuart G. Weekes, Oxford (GB); Graeme L. J. Paterson, Somerset (GB)

(73) Assignee: Powderject Research Limited (GB)

( * ) Notice: Subject to any disclaimer, the term of this patent is extended or adjusted under 35 U.S.C. 154(b) by 0 days.

(21) Appl. No.: 09/492,969

(22) Filed: Jan. 27, 2000

Related U.S. Application Data (60) Provisional application No. 60/117,806, filed on Jan. 29, 1999.

(51) Int. Cl.[7] .......................... A61M 13/00; A61M 5/30
(52) U.S. Cl. ............................................ 604/58; 604/70
(58) Field of Search ............................ 604/57, 58, 59, 604/60, 61, 62, 63, 64, 68, 69, 70, 71, 72, 87, 88, 131, 141, 143, 232, 290, 140

(56) References Cited

U.S. PATENT DOCUMENTS

| | | | | |
|---|---|---|---|---|
| 5,630,796 A | * | 5/1997 | Bellhouse et al. | .......... 604/518 |
| 6,004,286 A | * | 12/1999 | Bellhouse et al. | .......... 604/140 |
| 6,010,478 A | | 1/2000 | Bellhouse et al. | |
| 6,013,050 A | | 1/2000 | Bellhouse et al. | |
| 6,328,714 B1 | * | 12/2001 | Bellhouse et al. | .......... 604/232 |

FOREIGN PATENT DOCUMENTS

| | | |
|---|---|---|
| WO | WO 94/02188 | 2/1994 |
| WO | WO 96/04947 | 2/1996 |
| WO | WO 96/12513 | 5/1996 |
| WO | WO 96/20022 | 7/1996 |
| WO | WO 97/34652 | 9/1997 |
| WO | WO 97/47730 | 12/1997 |
| WO | WO 98/57691 | 12/1998 |

* cited by examiner

*Primary Examiner*—Nicholas D. Lucchesi
*Assistant Examiner*—Mark K. Han
(74) *Attorney, Agent, or Firm*—Foley & Lardner, LLP (57) ABSTRACT

Replaceable components for use with a needleless syringe delivery device are provided. One replaceable component is a cartridge having a source of particles and a source of compressed gas. Another replaceable component is a nozzle assembly having a particle acceleration nozzle and a coaxial filter element. Reusable needleless syringe devices which include these replaceable components are also provided.

6 Claims, 4 Drawing Sheets

PARTICLE DELIVERY DEVICE

CROSS-REFERENCE TO RELATED APPLICATION

This application is related to U.S. provisional patent application Ser. No. 60/117,806, filed 29 Jan. 1999, from which application priority is claimed pursuant to 35 U.S.C. §119(e)(1) and which application is incorporated herein by reference in its entirety.

TECHNICAL FIELD

The invention relates generally to a needleless syringe for use in delivery of particles of a therapeutic agent to a target surface. More particularly, the invention pertains to a reusable needleless syringe system that uses a replaceable cartridge unit having a sealed chamber, a source of particles of a therapeutic agent, and a source of a driving gas contained at super-atmospheric pressure. The invention further pertains to a reusable needleless syringe system that uses a replaceable nozzle assembly.

BACKGROUND

In commonly-owned U.S. Pat. No. 5,630,796 to Bellhouse et al., a non-invasive delivery system is described that entails the use of a needleless syringe. The syringe is used for transdermal delivery of powdered therapeutic compounds and compositions to skin, muscle, blood or lymph. The syringe can also be used in conjunction with surgery to deliver therapeutics to organ surfaces, solid tumors and/or to surgical cavities (e.g., tumor beds or cavities after tumor resection).

The needleless syringe is constructed as an elongate tubular nozzle, typically having a rupturable membrane initially closing the passage through the nozzle adjacent to the upstream end of the nozzle. Particles of a powdered therapeutic agent are located adjacent to the membrane. The therapeutic agent is delivered using an energizing means which applies a gaseous pressure to the upstream side of the membrane that is sufficient to burst the membrane, thereby producing a supersonic gas flow through the nozzle. The supersonic gas flow produced in the nozzle entrains the particles and accelerates them to suitable velocities for transdermal delivery into tissue such as skin or muscle.

SUMMARY OF THE INVENTION

It is a primary object of the invention to provide a reusable needleless syringe device that employs one or more replaceable components. Accordingly, in one aspect of the invention, a replaceable cartridge is provided for use in a needleless syringe. The replaceable cartridge is formed from a housing having a top end and a bottom end, wherein the bottom end has an inlet aperture and an outlet aperture that are side-by-side and in fluid communication with each other by way of an internal gas passageway which extends through the housing. The cartridge further includes a particle container containing a suitable amount of particles for a single therapeutic or diagnostic particle administration. The particle container is arranged within the housing and positioned over the outlet. The cartridge also contains a source of compressed gas, again suitable for powering a single therapeutic or diagnostic particle administration. The source of compressed case is arranged in sealable communication with the inlet, wherein the source includes an exterior portion which extends away from the housing and an interior portion which extends through the inlet and partially into the gas passageway such that a breach can be made to the interior portion in order to release compressed gas from the source and into the gas passageway.

In one configuration of the replaceable cartridge, the internal gas passageway is substantially in the shape of a U. In addition, the replaceable cartridge can accommodate an inserted expansion chamber at the downstream end of the gas passageway, or the housing can be molded or otherwise constructed to include an expansion chamber portion within the gas passageway. A filter element can likewise be included within the gas passageway.

In another aspect of the invention, a replaceable nozzle assembly is provided for use in a needleless syringe. The replaceable nozzle assembly includes an elongate particle acceleration nozzle having an upstream end, a downstream end and a gas passageway extending between the upstream and downstream ends. The gas passageway has an upper convergent section, a lower divergent section, and a throat section connecting the convergent and divergent sections. An outwardly projecting, disk-shaped annular flange is provided at the upstream terminus of the nozzle, which flange provides an external shoulder. The nozzle assembly further includes a cylindrical filter element which fits over and substantially surrounds the elongate particle acceleration nozzle. The filter element is separately replaceable from the nozzle. The filter element rests upon the external shoulder provided by the flange. The filter element includes a filter medium which provides a barrier against fine particles which, having insufficient momentum, may rebound from the target surface during or shortly after a particle delivery operation has been carried out.

In a still further aspect of the invention, a reusable needleless syringe device is provided. The reusable needleless syringe contains either or both the replaceable cartridge and the replaceable nozzle assembly of the present invention.

It is an advantage of the invention that a reusable needleless syringe can be provided which allows for multiple particle delivery operations to be carried out. It is a further advantage of the invention that the replaceable cartridges and nozzle assemblies of the present invention can be easily mass produced, packaged, stored, handled and then disposed of, significantly reducing the per-shot cost of operating a needleless syringe device.

These and other objects, aspects, embodiments and advantages of the present invention will readily occur to those of ordinary skill in the art in view of the disclosure herein.

DETAILED DESCRIPTION OF THE PREFERRED EMBODIMENTS

Before describing the present invention in detail, it is to be understood that this invention is not limited to particularly exemplified device structures as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, reference to "a therapeutic agent" includes a mixture of two or more such agents, reference to "a gas" includes mixtures of two or more gases, and the like.

A. Definitions

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed, and are intended to be defined as indicated below.

The terms "needleless syringe," and "needleless syringe device," as used herein, expressly refer to a particle delivery system that can be used to deliver particles into and/or across tissue, wherein the particles have an average size ranging from about 0.1 to 250 μm, preferably about 10–70 μm. Particles larger than about 250 μm can also be delivered from these devices, with the upper limitation being the point at which the size of the particles would cause untoward pain and/or damage to the target tissue. The particles are delivered at high velocity, for example at velocities of at least about 150 m/s or more, and more typically at velocities of about 250–300 m/s or greater. Such needleless syringe devices were first described in commonly-owned U.S. Pat. No. 5,630,796 to Bellhouse et al., incorporated herein by reference, and have since been described in commonly owned International Publication Nos. WO 96/04947, WO 96/12513, and WO 96/20022, all of which publications are also incorporated herein by reference. These devices can be used in the transdermal delivery of a therapeutic agent through skin or mucosal tissue, either in vitro or in vivo (in situ); or the devices can be used in the transdermal delivery of generally inert particles for the purpose of non- or minimally invasive sampling of an analyte from a biological system. Since the term only relates to devices which are suitable for delivery of particulate materials, devices such as liquid-jet injectors are expressly excluded from the definition of a "needleless syringe."

The term "transdermal" delivery captures intradermal, transdermal (or "percutaneous") and transmucosal administration, i.e., delivery by passage of a therapeutic agent into and/or through skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and *Transdermal Delivery of Drugs*, Vols. 1–3, Kydonieus and Berner (eds.), CRC Press, (1987). Aspects of the invention which are described herein in the context of "transdermal" delivery, unless otherwise specified, are meant to apply to intradermal, transdermal and transmucosal delivery. That is, the devices, systems, and methods of the invention, unless explicitly stated otherwise, should be presumed to be equally applicable to intradermal, transdermal and transmucosal modes of delivery.

As used herein, the terms "therapeutic agent" and/or "particles of a therapeutic agent" intend any compound or composition of matter which, when administered to an organism (human or animal) induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, biological response modifiers, nucleic acids, gene constructs and the like. More particularly, the term "therapeutic agent" includes compounds or compositions for use in all of the major therapeutic areas including, but not limited to, adjuvants, anti-infectives such as antibiotics and antiviral agents; analgesics and analgesic combinations; local and general anesthetics; anorexics; antiarthritics; anti-asthmatic agents; anticonvulsants; antidepressants; antigens, antihistamines; anti-inflammatory agents; antinauseants; antineoplastics; antipruritics; antipsychotics; antipyretics; antispasmodics; cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins peptides and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like).

Particles of a therapeutic agent, alone or in combination with other drugs or agents, are typically prepared as pharmaceutical compositions which can contain one or more added materials such as carriers, vehicles, and/or excipients. "Carriers," "vehicles" and "excipients" generally refer to substantially inert materials which are nontoxic and do not interact with other components of the composition in a deleterious manner. These materials can be used to increase the amount of solids in particulate pharmaceutical compositions. Examples of suitable carriers include water, silicone, gelatin, waxes, and like materials. Examples of normally employed "excipients," include pharmaceutical grades of dextrose, sucrose, lactose, trehalose, mannitol, sorbitol, inositol, dextran, starch, cellulose, sodium or calcium phosphates, calcium sulfate, citric acid, tartaric acid, glycine, high molecular weight polyethylene glycols (PEG), and combinations thereof. In addition, it may be desirable to include a charged lipid and/or detergent in the pharmaceutical compositions. Such materials can be used as stabilizers, anti-oxidants, or used to reduce the possibility of local irritation at the site of administration. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, e.g., TWEEN® surfactants (Atlas Chemical Industries, Wilmington, Del.), polyoxyethylene ethers, e.g., Brij, pharmaceutically acceptable fatty acid esters, e.g., lauryl sulfate and salts thereof (SDS), and like materials.

The term "analyte" is used herein in its broadest sense to denote any specific substance or component that one desires to detect and/or measure in a physical, chemical, biochemical, electrochemical, photochemical, spectrophotometric, polarimetric, calorimetric, or radiometric analysis. A detectable signal can be obtained, either directly or indirectly, from such a material. In some applications, the analyte is a physiological analyte of interest (e.g., a physiologically active material), for example glucose, or a chemical that has a physiological action, for example a drug or pharmacological agent.

As used herein, the term "sampling" means extraction of a substance from any biological system across a membrane, generally across skin or tissue. The membrane can be natural or artificial, and is generally animal in nature, such as natural or artificial skin, blood vessel tissue, intestinal tissue, and the like. A "biological system" thus includes both living and artificially maintained systems.

B. General Methods

In one embodiment, a replaceable cartridge for use with a reusable needleless syringe is provided. The replaceable cartridge contains both a source of particles and a source of compressed gas, and is intended as a single-use disposable cartridge. In another embodiment, a replaceable nozzle assembly for use with a reusable needleless syringe is provide. The replaceable nozzle assembly includes a supersonic particle acceleration nozzle and a filter element which surrounds the acceleration nozzle. In a still further embodiment, a reusable needleless syringe is provided which contains either one or both of the above-described replaceable components.

Needleless syringe devices for delivering particles were first described in commonly owned U.S. Pat. No. 5,630,796 to Bellhouse et al., incorporated herein by reference. Although a number of specific device configurations are now available, such devices are typically provided as a pen-shaped instrument containing, in linear order moving from top to bottom, a gas cylinder, a particle cassette or package, and a supersonic nozzle with an associated silencer medium. An appropriate powder is sealed within a particle cassette, e.g., a container formed by two rupturable polymer membranes that are heat-sealed to a washer-shaped spacer to form a self-contained sealed unit. The membrane material is selected to achieve a specific mode of opening and burst pressure that dictates the conditions at which the supersonic flow is initiated. In operation, the device is actuated to release the compressed gas from the cylinder into an expansion chamber within the device. The released gas contacts the particle cassette and, when sufficient pressure is built up, suddenly breaches the cassette membranes sweeping the particles into the supersonic nozzle for subsequent delivery. The nozzle is designed to achieve a specific gas velocity and flow pattern to deliver a quantity of particles to a target surface of predefined area. The silencer is used to attenuate the noise of the "sonic boom" produced by the membrane rupture. Such devices are most commonly manufactured as a disposable unit, and the spent devices are intended to be discarded after a single particle delivery operation has been carried out. Accordingly, these devices are typically inexpensively manufactured from medical grade plastics using injection-molding techniques (with the exception of the gas cylinder which is typically deep-drawn from aluminum or some other suitable metal or metal alloy) to facilitate such single use economics.

Figure 1:
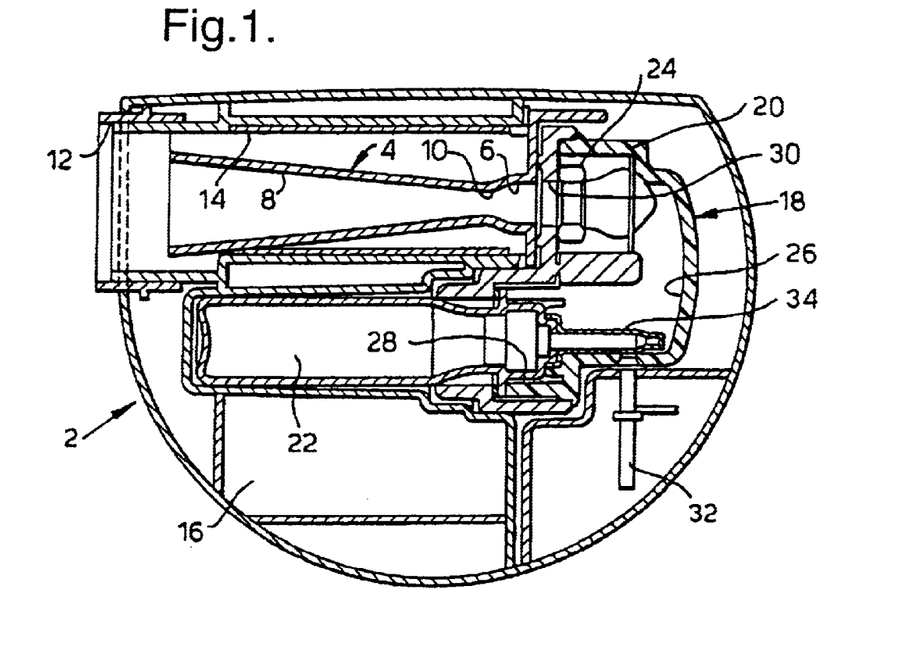
FIG. 1 is a cross-sectional view of a reusable needleless syringe device containing a replaceable nozzle assembly and a replaceable cartridge, both of which replaceable components are constructed according to the present invention.
Figure 2:
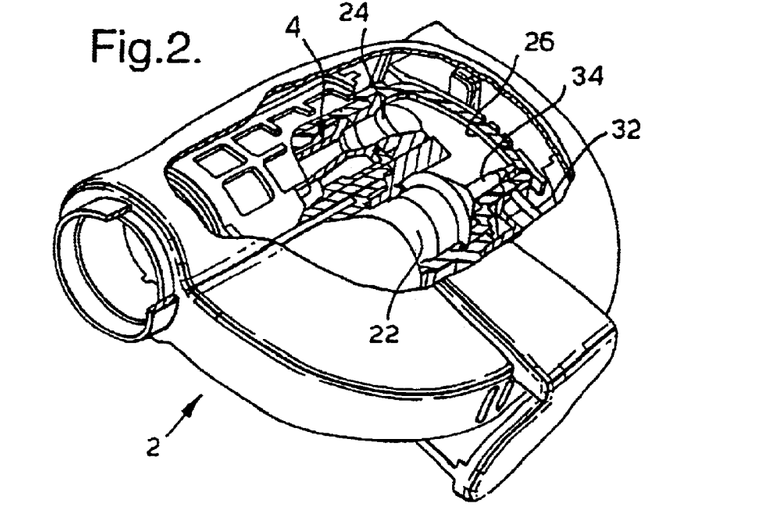
FIG. 2 is a pictorial representation of the reusable needleless syringe device of FIG. 1 shown in partial cut-away to illustrate the working components of the device.

The reusable needleless syringes of the present invention contain the same basic elements and function in the same basic manner as the above-described devices. However, these reusable devices are specially configured to accommodate multiple use by either medical personnel or consumers, and contain replaceable components such as a cartridge containing fresh particle cassette with a gas cylinder, or a new nozzle unit. One particular reusable needleless syringe device is depicted in FIGS. 1 and 2. As can be seen, this particular reusable device is not arranged in the typical linear "pen-shaped" configuration, rather the device has been bent around into a U-shape to place the nozzle and gas cylinder into a "side-by-side" orientation, substantially shortening the overall length of the device.

Referring particularly to FIG. 1, the reusable device 2 includes a replaceable nozzle assembly generally indicated at 4 which has a supersonic particle acceleration nozzle. The particle acceleration nozzle has an upper convergent section 6, a lower divergent section 8, and a throat section 10 connecting the convergent and divergent sections. The particle acceleration nozzle terminates at its downstream end within a spacer shroud 12 that is-provided by the reusable device 2. The shroud is intended to be pressed against a target surface to create a suitable seal and to space the nozzle at a preselected distance from the surface to optimize particle delivery conditions. The outside of the nozzle assembly 4 is surrounded by a filter element 14 that is intended to capture and contain any particle "fines" that may rebound from the target surface and be dispersed within the spacer shroud and nozzle assembly immediately after delivery. The shroud is further intended to capture the shockwave that is reflected from the target surface, which shockwave can then travel radially outwards from the shroud through appropriate vents and pass into a silencer chamber 16 for sound attenuation. As will be described in greater detail herein below, the filter element 14 can be easily disconnected from the rest of the nozzle assembly 4 and thus replaced separately.

The reusable device 2 further includes a replaceable cartridge 18 which comprises a housing 20, a source of compressed gas 22, and a particle container 24 which contains particles. The housing 20 provides an enclosed structure having an internal gas passageway 26 which connects an inlet aperture 28 and an outlet aperture 30 which are disposed on the same bottom side of the housing. The source of compressed gas 22 is inserted into the inlet aperture 28 such that a top portion of the source extends partially into the internal gas passageway 26. Insertion of the gas source, in this case, a gas cylinder, into the inlet aperture closes off the inlet and provides a gas-tight seal. Similarly, the particle container 24 is positioned over and blocks off the outlet aperture 30 also creating a gas-tight seal. In this way, the replaceable cartridge 18 is an entirely self-contained, integral component which provides both the particles and the source of motive force necessary for a single operation of the reusable needleless syringe device. The particle container 24 can comprise any suitable structure which can effectively contain a metered amount of particles. However, in the particular embodiment depicted in FIG. 1, the particle container is a capsule formed from two comparatively weak, rupturable membranes which are attached to a spacer ring to establish a self-contained unit as described in U.S. Pat. No. 5,630,796. The rupturable membranes are formed from a suitable polymer material, for example polycarbonates (e.g., Macrafol™), MYLAR® or other like materials. Both the membrane material and the thickness of the membrane material are selected to provide for a specific mode of opening and burst pressure as also previously described.

Referring now to FIGS. 1 and 2, the reusable device is operated by creating a breach in the top portion of the gas source 22 such that the compressed gas can escape from the source and enter into the internal gas passageway 26. In the particular embodiment depicted in FIGS. 1 and 2, the breach is created by the action of a actuation ram or pin 32 which is used to snap off a frangible tip 34 from the inner portion of the gas source. In this manner, the compressed gas flows into the internal gas passageway 26 where it is initially retained by the upstream membrane of the particle container 24. After sufficient pressure has built up within the gas passageway, the rupturable membranes of the particle container are burst, allowing the gas to sweep through the container and entrain the particles within the gas flow entering the supersonic particle acceleration nozzle of the nozzle assembly 4. A number of alternative actuation mechanisms can, of course be used to create the breach in the gas source. For example, a sharp pin or needle can be used to pierce a hole in the gas source or rupture a membrane or other relatively weak portion of the gas source. Alternatively, a trigger mechanism can be used to open a valve which closes off the gas source. These and other suitable actuation schemes and mechanisms will readily occur to the ordinarily skilled artisan upon reading the instant specification. After the device has been operated, the spent cartridge 18 can be removed from the reusable device 2 and replaced with a fresh cartridge which contains a new gas source and particle container. In like manner, the nozzle assembly 4 can be removed, and either the filter element 14, or the entire nozzle assembly can be replaced with fresh components.

Figure 3:
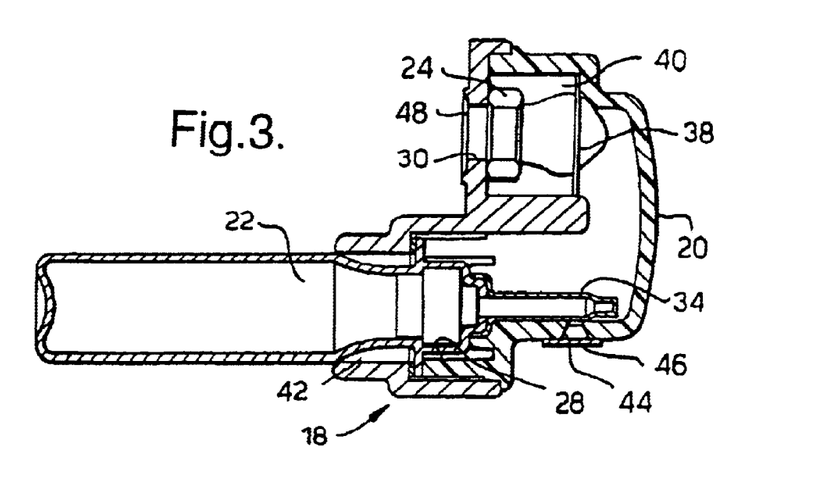
FIG. 3 is a cross-sectional view of a replaceable cartridge constructed according to the invention.
Figure 6:
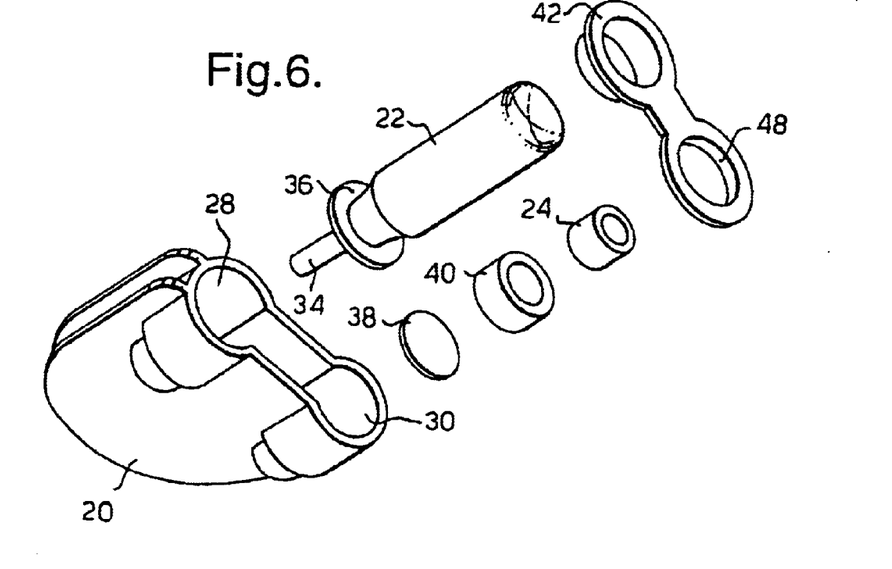
FIG. 6 is an exploded view of the replaceable cartridge of FIG. 3.

FIGS. 3–7 depict the construction and assembly of a replaceable cartridge 18 which is suitable for use in the reusable needleless syringe devices of the present invention. Referring particularly to FIGS. 3 and 6, the cartridge housing 20 is roughly in the shape of a D and has inlet and outlet apertures, 28 and 30, respectively, positioned on the bottom end thereof. The housing can be made from any suitably resilient material, preferably from a medical-grade plastic which may be injection-molded into any suitable configuration.

During assembly, a fresh gas source 22 is inserted into the inlet aperture 28. The gas source can have a flange 36 which rests against a corresponding shoulder within the housing in order to position the tip 34 within the gas passageway 26 as previously described. When the cartridge is fully assembled, this flange helps provide for a gas-tight seal. The gas source 22 can be any suitable container of compressed air or gas, and typically will be charged at about 10–100 bar or more, more typically at about 25–60 bar. The top end of the cartridge housing 20 is hollow in order to establish an intermediate portion of the gas passageway, and is typically somewhat pinched and narrow as best seen in the top view provided by FIG. 5. The gas passageway 26 is substantially in the shape of a U. An optional internal filter element 38 can be arranged within the internal gas passageway 26 in order to prevent fragments or bits from the breached gas source from entering into the nozzle assembly. The internal filter element is preferably arranged at or near the outlet aperture 30, and can be made from any suitable filtering material, for example a stainless steel mesh or fabric material that allows free passage of the compressed gas but retains any fragments or particles which could enter into the gas passageway during operation of the device. The internal filter element 38 can rest upon an internal shoulder provided within the housing, or can be positioned and retained by any suitable means.

The cartridge housing 20 can be manufactured to provide an expansion chamber portion within the gas passageway, at a location adjacent to the outlet aperture 30. In this regard, the expansion chamber portion is configured to have an increased cross-sectional area relative to the intermediate portion of the passageway, and thus allows for the creation of an increased pressure front immediately above the particle source 24 in order to facilitate operation of the device. However, it is preferred that an expansion chamber insert 40 be used to provide this function, wherein the insert can be a simple molded annular part having a suitable convergent inner geometry.

Accordingly, during assembly, the internal filter element can be dropped into the outlet aperture 30 and rests upon an internal shoulder. The expansion chamber insert 40 can then be inserted, and the particle container 24 finally added to block off the outlet aperture. A bottom casement 42 can then be snapped into place or otherwise attached to the housing 20 in order to hold the various components together as a fully assembled, gas-tight replaceable cartridge. As can be seen in FIG. 3, the bottom casement 42 can optionally have an outlet aperture portion 48 which provides an annular female lip at the terminus of the outlet aperture 30 in the assembled cartridge. This annular lip accepts and closely engages a corresponding annular male flange provided at the top of a nozzle assembly, thus positioning the particle container immediately over the entrance of the particle acceleration nozzle and providing a tight seal between the two elements.

Figure 4:
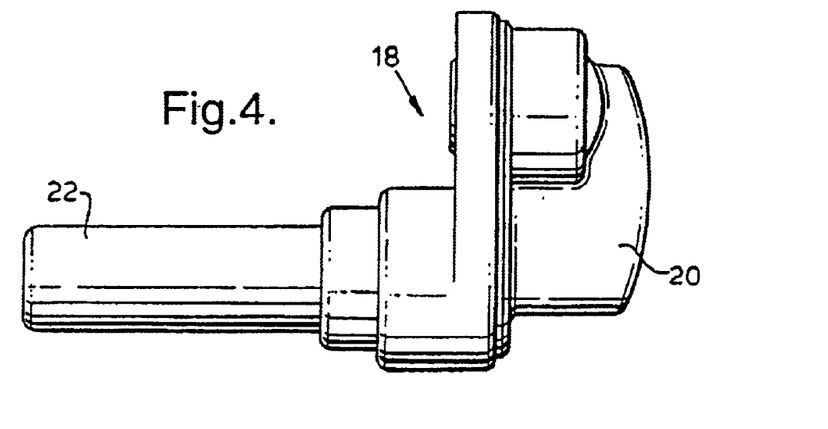
FIG. 4 is a side plan view of the replaceable cartridge of FIG. 3.
Figure 5:
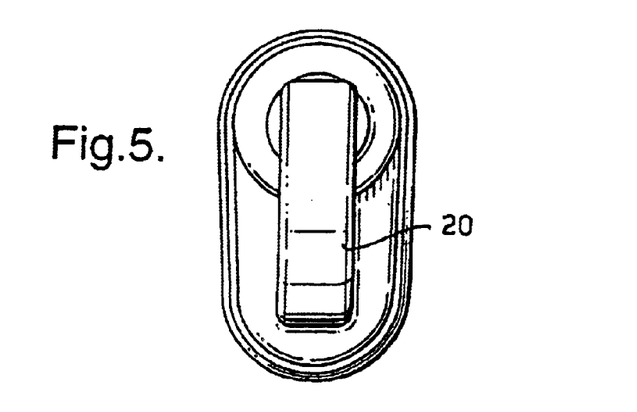
FIG. 5 is a top plan view of the replaceable cartridge of FIG. 3.

Referring particularly to FIGS. 3 and 4, when the cartridge has been assembled, an interior portion of the gas source 22 extends partially into the gas passageway 26, and an exterior portion of the gas source extends away from the housing 20. Part of the interior portion of the gas source is comprised of a frangible, elongate tip 34 which is position in the assembled cartridge so that it is adjacent to an actuation aperture 44. The actuation aperture is sized to allow an actuation ram or pin to travel into the housing and break off the frangible tip during actuation of the device. The actuation aperture 44 is sealed off by a pierceable foil or seal 46 which is applied to the outside of the housing as seen in FIG. 3. This seal provides for an intuitive indicator of when a cartridge has been spent, since the seal on a used cartridge will be breached.

Figure 7:
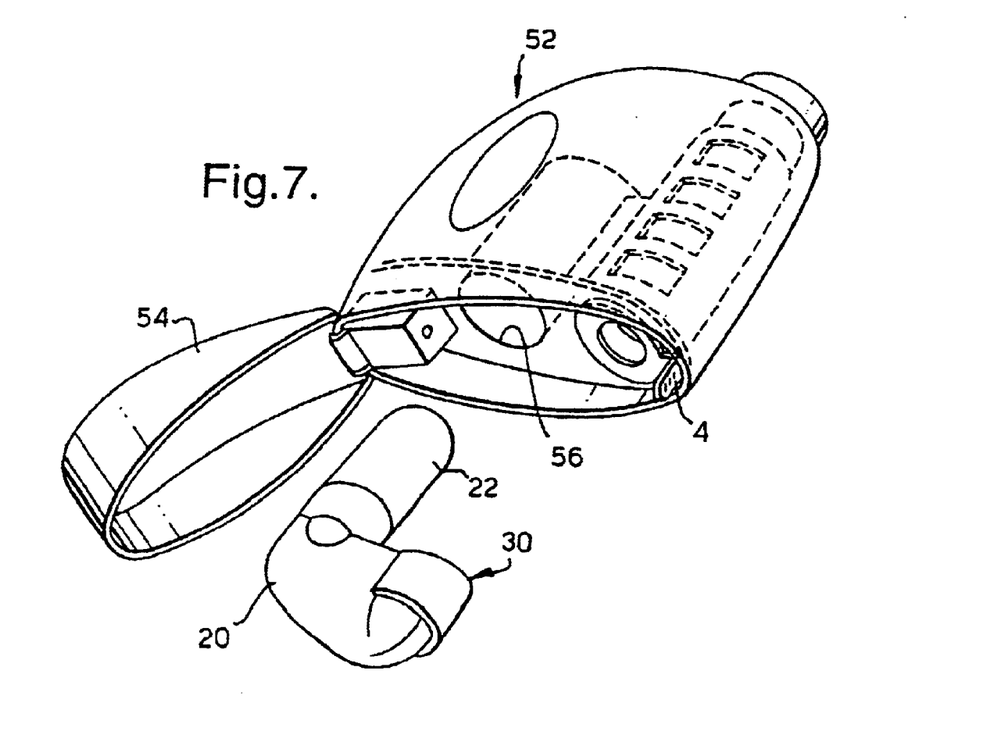
FIG. 7 is a pictorial representation depicting the replaceable cartridge of FIG. 3 being inserted into a reusable needleless syringe device similar to the device of FIGS. 1 and 2.

The fully assembled replaceable cartridge is inserted into a reusable needleless syringe device as follows. Referring particularly to FIG. 7, the back cover 54 of a reusable needleless syringe device 52 is opened to reveal a cavity 56 and the top end of a replaceable nozzle assembly 4. The exterior portion of the gas source 22 fits into the cavity 56 and the outlet aperture 30 couples with the top of the nozzle assembly 4. The cover 54 is then closed to provide a fully ready and operational device.

Other embodiments of the replaceable cartridge of the present invention are those which can be used with the more standard, linear "pen-shaped" devices such as the needleless syringe devices disclosed in U.S. Pat. No. 5,630,796 to Bellhouse et al. Accordingly, in such alternative embodiments, the cartridge will have an overall cylindrical configuration, with the various components being provided in a linear arrangement. Such cartridges can be thought of as a shotgun shell, wherein a source of motive force (the gas source) is positioned behind a particle container and both elements are encased by an easy to handle outer housing. One particular arrangement comprises a housing having, in linear arrangement in the order listed, an upstream gas source (e.g., a cartridge containing compressed gas or air), an intermediate gas passageway including an expansion chamber, and a downstream particle container. Optional elements, such as an internal filter or an inserted expansion chamber, can be included as described above for the side-by-side cartridge. The gas source can be fully contained within the housing or, alternatively, have an interior portion extending partially into the gas passageway and an external portion extending away from the housing as also described above. In this manner, a breach can be made to the interior portion of the gas source in order to actuate a particle delivery operation.

Figure 8:
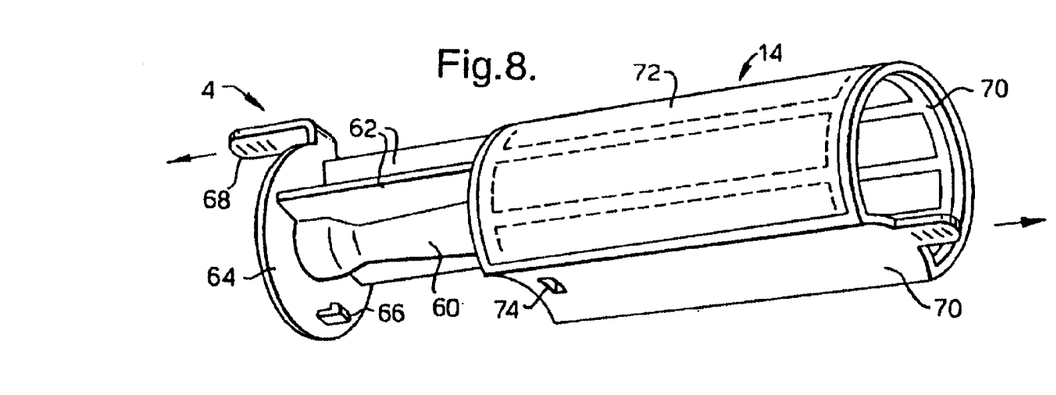
FIG. 8 is a side plan view of a replaceable nozzle assembly constructed according to the present invention, wherein the assembly is shown in partial exploded view.
Figure 9:
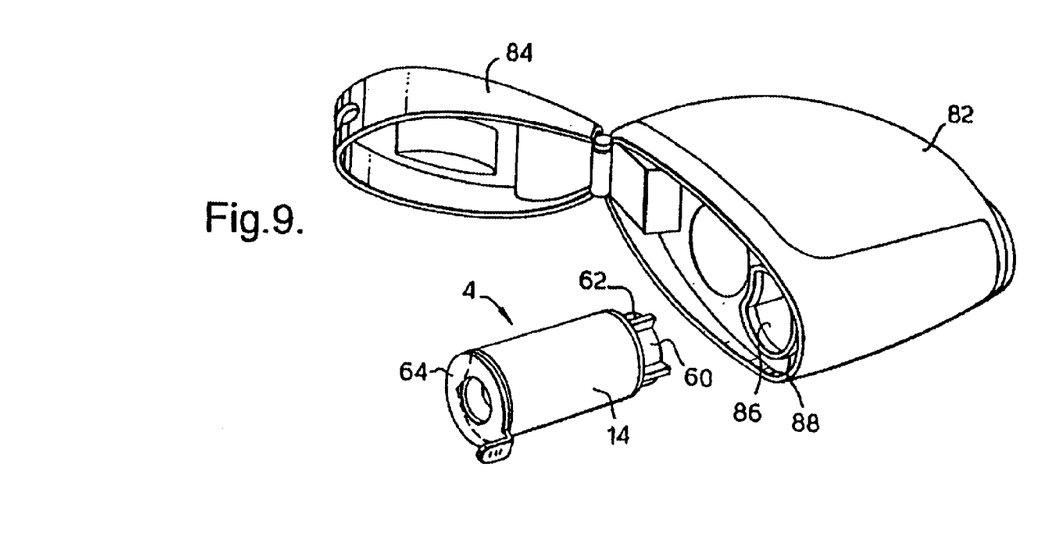
FIG. 9 is a pictorial representation depicting the replaceable nozzle assembly of FIG. 8 being inserted into a reusable needleless syringe device similar to the device of FIGS. 1 and 2.

FIGS. 8 and 9 depict the construction and assembly of a replaceable nozzle assembly 4 which is suitable for use in the reusable needleless syringe devices of the present invention. Referring particularly to FIG. 8, the replaceable nozzle assembly 4 comprises an elongate particle acceleration nozzle 60 and a cylindrical filter element 14 which is inserted over and substantially surrounds the particle acceleration nozzle. The particle acceleration nozzle 60 can have one or more outwardly projecting fins 62 depending from the exterior surface thereof, which fins may provide structural rigidity to the nozzle itself and/or establish a support for the cylindrical filter element. The passageway through the nozzle has an upstream convergent section, a downstream divergent section, and a throat section interposed between the convergent and divergent sections. The particle acceleration nozzle can be formed from any suitably resilient material which can be machined and/or molded to provide both the desired external features, e.g., the outwardly projecting fins 62 and the desired external features, e.g., the convergent, divergent nozzle geometries. It is preferred that the nozzle is injection-molded from a suitable medical grade of plastic. The particle acceleration nozzle further comprises an outwardly projecting disc-shaped flange 64 depending from its upstream end to provide an external shoulder. The flange 64 may optionally have a finger or clip 66 extending therefrom in a downstream direction and providing a point of engagement for the filter element 14 as described herein below. The flange 64 may also have a grip or tab 68 extending therefrom in an upstream direction, which grip or tab provides an intuitive element for grasping the replaceable nozzle assembly 4 and removing the same when the assembly is properly positioned in a reusable needleless syringe.

The filter element 14 comprises a cylindrical carrier moulding 70 which is sized to fit around and substantially surround the elongate particle acceleration nozzle 60 along most of its length. The carrier moulding 70 is preferably constructed as an open structure, for example any honeycomb, scaffold, lattice or otherwise open-frame construction which provides for as much open area about its periphery as possible. The carrier moulding can be formed from any suitable material such as a metal, plastic, rigid paper, cardboard or pressed-fiber material. A filter medium 72 is wrapped around the carrier molding and establishes a barrier against reflected particles and/or particle "fines" that, having insufficient momentum to penetrate the intended target, may rebound from the target surface during or just after particle delivery from a needleless syringe. This helps prevent such particles or particle fines from entering into inappropriate parts of the reusable device, particularly from entering into the silencing medium generally used with needleless syringe devices which silencing medium comprises an open-cell foam material. The filter medium is selected to have a very small pore size and can thus be formed from a paper, fiber, or paper/fiber filter sheet similar to a coffee filter. If desired, the carrier moulding 70 can have a notch or other fastener mechanism 74 that cooperates with the corresponding finger or clip 66 on the nozzle flange 64. The replaceable nozzle assembly is put together by sliding the cylindrical carrier molding over the outside of the nozzle 60, generally using the fins 62 to guide and support the carrier until it is brought to rest against the shoulder provided by the flange 64. The two elements can be held together as a complete nozzle assembly by way of establishing a tight fit tolerance between the outside dimension of the particle acceleration nozzle 60, e.g., the outermost edges of the fins 62, and the inside dimension of the carrier moulding 70. Alternatively or additionally, the two elements can be held together by a latch or fastening mechanism provided by one or both of the carrier moulding and the nozzle, e.g., the corresponding structures 74 and 66 on each respective element. Removal of the filter element 14 from the particle acceleration nozzle 60 is carried out by pulling the two elements apart in the directions depicted by the right and left opposing arrows in FIG. 8. This allows the filter element to be replaced separately from, and possibly at more frequent intervals than the particle acceleration nozzle in a reusable needleless syringe device.

The fully assembled replaceable nozzle assembly is inserted into a reusable needleless syringe device as follows. Referring now to FIG. 9, the back cover 84 of a reusable needleless syringe device 82 is opened to reveal a cavity 86 which can accept and closely retain the nozzle assembly 4. If desired, a gasket 88 can be used to provide a tight seal between the flange 64 of the nozzle assembly and the case of the reusable needleless syringe device 82. The cover 84 is then closed to provide a fully ready and operational device. As will be understood by those skilled in the art upon reading the instant specification, the replaceable nozzle assembly of the present invention can be used with any reusable needleless syringe configuration, including the "side-by-side" configuration described herein, as well as the more traditional "pen-shaped" device as disclosed in U.S. Pat. No. 5,630,796 to Bellhouse et al.

Accordingly, novel replaceable components for use with a reusable needleless syringe system have been described, as well as reusable needleless syringe devices which comprise such replaceable components. Although preferred embodiments of the subject invention have been described in some detail, it is understood that obvious variations can be made without departing from the spirit and the scope of the invention as defined by the appended claims.

We claim:

1. A replaceable nozzle assembly for use in a needleless syringe, said nozzle assembly comprising:

(a) an elongate particle acceleration nozzle having an upstream end, a downstream end and a passageway extending between the upstream and downstream ends, wherein said passageway has an upper convergent section, a lower divergent section, and a throat section connecting the convergent and divergent sections, and further wherein said nozzle has an outwardly projecting annular flange depending from its upstream end to provide an external shoulder; and (b) a cylindrical particle filter medium which fits over and substantially surrounds the elongate particle acceleration nozzle and rests upon the external shoulder provided by the flange.

2. A reusable needleless syringe device comprising, in operative combination, a source of compressed gas, a particle container, and a nozzle comprising a cylindrical particle filter medium, said device further comprising a replaceable cartridge disposed within the device wherein said replaceable cartridge comprises:

(a) a housing having a top end and a bottom end, wherein the bottom end has an inlet aperture and an outlet aperture in fluid communication with each other by way of an internal gas passageway which extends through said housing;

(b) the particle container containing particles, said container arranged within the housing and positioned over the outlet; and (c) the source of compressed gas in sealable communication with the inlet, wherein said source of compressed gas includes an exterior portion which extends away from the housing and an interior portion which extends through the inlet and partially into the gas passageway such that a breach can be made to the interior portion in order to release compressed gas from the source and into the gas passageway.

3. The reusable needleless syringe device of claim 2 wherein the nozzle is disposed within a replaceable nozzle assembly.

4. The reusable needleless syringe device of claim 3 wherein said replaceable nozzle assembly comprises:

(a) the nozzle having an upstream end, a downstream end and a passageway extending between the upstream and downstream ends, wherein said passageway has an upper convergent section, a lower divergent section, and a throat section connecting the convergent and divergent sections, and further wherein said nozzle has an outwardly projecting annular flange depending from its upstream end to provide an external shoulder; and (b) the cylindrical particle filter medium, wherein the cylindrical particle filter medium fits over and substantially surrounds the nozzle and rests upon the external shoulder provided by the flange.

5. A reusable needleless syringe device comprising, in operative combination, a source of compressed gas, a particle container, and a nozzle, said device further comprising a replaceable nozzle assembly disposed within the device wherein said replaceable nozzle assembly comprises:

(a) the nozzle having an upstream end, a downstream end and a passageway extending between the upstream and downstream ends, wherein said passageway has an upper convergent section, a lower divergent section, and a throat section connecting the convergent and divergent sections, and further wherein said nozzle has an outwardly projecting annular flange depending from its upstream end to provide an external shoulder; and (b) a cylindrical particle filter medium which fits over and substantially surrounds the nozzle and rests upon the external shoulder provided by the flange.

6. The reusable needleless syringe device of claim 5 further comprising a replaceable cartridge disposed within the device, wherein said replaceable cartridge comprises:

(a) a housing having a top end and a bottom end, wherein the bottom end has an inlet aperture and an outlet aperture in fluid communication with each other by way of an internal gas passageway which extends through said housing;

(b) the particle container containing particles, said container arranged within the housing and positioned over the outlet; and (c) the source of compressed gas in sealable communication with the inlet, wherein said source of compressed gas includes an exterior portion which extends away from the housing and an interior portion which extends through the inlet and partially into the gas passageway such that a breach can be made to the interior portion in order to release compressed gas from the source and into the gas passageway.

* * * * *